United States Patent
Andersen et al.

(10) Patent No.: US 9,732,331 B2
(45) Date of Patent: Aug. 15, 2017

(54) **CODON MODIFIED AMYLASE FROM *BACILLUS AKIBAI***

(71) Applicant: Novozymes A/S, Bagsvaerd (DK)

(72) Inventors: Jens Toenne Andersen, Bagsvaerd (DK); Niels Banke, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/898,502

(22) PCT Filed: Jun. 17, 2014

(86) PCT No.: PCT/EP2014/062665
§ 371 (c)(1),
(2) Date: Dec. 15, 2015

(87) PCT Pub. No.: WO2014/206806
PCT Pub. Date: Dec. 31, 2014

(65) Prior Publication Data
US 2016/0115463 A1    Apr. 28, 2016

(30) Foreign Application Priority Data
Jun. 24, 2013   (EP) ..................... 13173431

(51) Int. Cl.
*C12N 15/56*    (2006.01)
*C12N 9/28*    (2006.01)

(52) U.S. Cl.
CPC .... *C12N 9/2417* (2013.01); *C12Y 302/01001* (2013.01)

(58) Field of Classification Search
None
See application file for complete search history.

(56) References Cited

FOREIGN PATENT DOCUMENTS

WO    2013/063460 A2    5/2013

OTHER PUBLICATIONS

Neilson et al., Biochimica et Biophysica Acta, vol. 1543, pp. 253-274 (2000).
Nelch et al., PLoS One, vol. 4, Issue 9, Article e7002, pp. 1-10 (2009).

*Primary Examiner* — Rebecca Prouty
(74) *Attorney, Agent, or Firm* — Elias Lambiris

(57) ABSTRACT

The present invention relates to an isolated synthetic polynucleotide encoding the mature amylase AX856 from *Bacillus akibai*, using codon modified polynucleotide constructs for the expression of the amylase.

20 Claims, No Drawings

US 9,732,331 B2

CODON MODIFIED AMYLASE FROM *BACILLUS AKIBAI*

CROSS-REFERENCE TO RELATED APPLICATIONS

This application is a 35 U.S.C. 371 national application of international application no. PCT/EP2014/062665 filed Jun. 17, 2014, which claims priority or the benefit under 35 U.S.C. 119 of European application no. 13173431.1 filed Jun. 24, 2013. The content of each application is fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to an isolated synthetic polynucleotide encoding a mature amylase, a polynucleotide construct comprising the polynucleotide, a recombinant host cell transformed with or comprising said polynucleotide or polynucleotide construct and a method for producing the mature amylase, said method comprising the step of cultivating the host cell as under conditions conducive for the expression of the amylase.

BACKGROUND OF THE INVENTION

In the highly competitive industrial manufacture of enzymes it is of vital importance to constantly improve yield or productivity. Genetic manipulation or engineering has been put to use for this purpose for many years, where genes encoding polypeptides of interest have been placed under the transcriptional control of heterologous or synthetic promoters, they have been expressed with heterologous signal peptides in various host cells and they have been integrated in the host cell genomes in multiple copies in order to achieve so-called mRNA-saturation.

Another well-known technique to increase enzyme productivity has been to optimize the codon-usage in enzyme-encoding DNA sequence based on that of the host cell intended for its expression and based on various theoretical mRNA melting point or tertiary structure calculations.

Even so, it remains of significant interest to identify new ways to improve the expression of an enzyme of interest. Due to the highly competitive environment in the enzyme manufacture industry, even minor improvements are desirable.

SUMMARY OF THE INVENTION

We constructed a *Bacillus licheniformis* parent host strain for the site-specific integration of three identical copies of a polynucleotide encoding a mature amylase polypeptide of interest fused with the heterologous signal peptide from the AmyL amylase.

Four progeny strains were then constructed by introducing into the parent strain three identical copies of the native *Bacillus akibai* AX856 mature amylase-encoding gene (SEQ ID NO:1) as well as three different synthetic codon-optimized versions of the AX856 amylase-encoding gene: Syn1 (SEQ ID NO:2), Syn2 (SEQ ID NO:3) and Syn3 (SEQ ID NO:4), respectively. To our surprise, one of the synthetic genes, Syn3 (SEQ ID NO:4), vastly outperformed the two other synthetic genes by almost a factor of two.

Accordingly, in a first aspect the invention provides an isolated synthetic polynucleotide encoding a mature amylase, said polynucleotide comprising the nucleotide sequence shown in SEQ ID NO:4.

In a second aspect, the invention relates to a polynucleotide construct comprising a polynucleotide as defined in the first aspect operably ed to control sequences that provide for its expression in a host cell of choice.

In a third aspect, the invention relates to a recombinant host cell transformed with or comprising a polynucleotide as defined in the first aspect or a polynucleotide construct as defined in the second aspect, wherein said host cell produces the mature amylase.

In a final aspect, the invention relates to a method for producing a mature amylase, said method comprising the steps of:
 a) cultivating a host cell as defined in the third aspect under conditions conducive for the expression of the amylase; and optionally
 b) recovering the amylase.

Definitions

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is encoded by a polynucleotide having the DNA sequence shown in SEQ ID NO: 4. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide. In one aspect, the mature polypeptide coding sequence is SEQ ID NO: 4.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

DETAILED DESCRIPTION OF THE INVENTION

Polynucleotides

The present invention also relates to isolated polynucleotides encoding a mature amylase polypeptide as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used. The native amylase-encoding polynucleotide may be cloned from a strain of *Bacillus akibai* using well-known methods.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 4, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Accordingly, in a first aspect the invention relates to an isolated synthetic polynucleotide encoding a mature amylase, said polynucleotide comprising the nucleotide sequence shown in SEQ ID NO:4; preferably the isolated synthetic polynucleotide consists of the nucleotide sequence shown in SEQ ID NO:4.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. Other examples of regulatory sequences are those that allow for gene amplification.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Accordingly, in a second aspect the invention relates to a polynucleotide construct comprising a polynucleotide as defined in the first aspect, operably linked to control sequences that provide for its expression in a host cell of choice; preferably the control sequences comprise a triple tandem promoter; more preferably the control sequences comprise a polynucleotide region that encodes a signal peptide fused to the N-terminus of the amylase which directs the amylase into the secretory pathway of the host cell; and most preferably the signal peptide is the amyL signal peptide.

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Strepto-*

*myces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

Accordingly, in a third aspect the invention relates to a recombinant host cell transformed with or comprising a polynucleotide as defined in the first aspect or a polynucleotide construct as defined in the second aspect, wherein said host cell produces the mature amylase.

Methods of Production

The present invention also relates to methods of producing a mature amylase encoded by the synthetic polynucleotide of the present invention, said method comprising the steps of:
a) cultivating a host cell as defined in the third aspect under conditions conducive for the expression of the amylase; and optionally
b) recovering the amylase.

In one preferred embodiment, the host cell is a *Bacillus* cell, including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for amylase enzymes. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

EXAMPLES

Example 1. Expression of Mature Amylase from Different Synthetic Genes

Strains:

A *Bacillus licheniformis* parent host strain was constructed for the site-specific integration of three identical copies of a polynucleotide encoding a polypeptide of interest. Four progeny strains were then constructed by introducing into the parent strain three identical copies of the native AX856 amylase-encoding gene as well as three different synthetic codon-optimized versions of the AX856 amylase-encoding gene, Syn1-Syn3, respectively:

*Bacillus licheniformis* PP3570 parent host strain.
*Bacillus licheniformis* JA 3716: (PP3570 transformed with native *Bacillus akibai* AX856 amylase gene).
*Bacillus licheniformis* JA 3718: (PP3570 transformed with Syn1 amylase gene).
*Bacillus licheniformis* JA 3720: (PP3570 transformed with Syn2 amylase gene).
*Bacillus licheniformis* JA 3722: (PP3570 transformed with Syn3 amylase gene).

Strain Constructions:
*Bacillus licheniformis* PP3570:

The parent *Bacillus licheniformis* strain PP3570 was constructed as follows: In a *Bacillus licheniformis* host the aprL, the glu specific protease mprL, sacB, the sigma F factor spo2AC and cypX genes were deleted. The forD translation was disrupted by mutations in the Ribosomal Binding Site (RBS).

The resulting strain was further modified by site-specifically inserting copies of a strong triple tandem promoter (as disclosed in WO9943835) in three separate loci on the chromosome Into each of the three loci an additional DNA was then inserted containing the attB site from Lactococcal phage TP901-1. The attB recognition sequence is used for simultaneous insertion of a copy of a polynucleotide encoding a polypeptide of interest into the three loci on the chromosome so they end up being operably linked by the triple tandem promoter already present in the loci. The insertion of the polynucleotide copies was done by transient expression of a phage TP901-1 recombinase as disclosed in WO06042548.

Using the parent strain and the phage integration approach we constructed the following four strains: JA3716, JA3718, JA3720 and JA3722, where all four are isogenic, except for the DNA sequence of the three inserted polynucleotide copies in each strain. The details of the strain constructions are provided below.

*Bacillus licheniformis* JA3716:

The gene encoding the *Bacillus akibai* amylase AX856 amylase was cloned into a phage integration vector, flanked downstream by an attP site for integration and upstream by the cry3A region, the latter intended for vector-only cross out by homologous recombination after integration of the full construct. The DNA sequence encoding the mature part of the amylase is shown in SEQ ID NO:1. The mature part of the amylase was expressed as a fusion polypeptide with the AmyL signal peptide. The resulting plasmid pJA3688 for inserting the amylase gene behind the triple tandem promoter region at the three attB sites on the parent *B. licheniformis* chromosome. The resulting 3-copy amylase strain was denoted JA3716.

The JA3716 strain has three copies of the polynucleotide of SEQ ID NO:1 encoding the mature amylase AX856 at three different positions in the chromosome.

*Bacillus licheniformis* JA3718:

A first synthetic codon-optimized gene (Syn1) encoding the AX856 amylase was cloned into a phage integration vector, flanked downstream by an attP site for integration and upstream by the cry3A region, the latter intended for vector-only cross out by homologous recombination after integration of the full construct. The DNA sequence encoding the mature part of the amylase is shown in SEQ ID NO:2. The mature part of the amylase was expressed as a fusion polypeptide with the AmyL signal peptide. The resulting plasmid pJA3691 for inserting the amylase gene behind the triple tandem promoter region at the three attB sites on the parent *B. licheniformis* chromosome. The resulting 3-copy amylase strain was denoted JA3718.

The JA3718 strain has three copies of the synthetic polynucleotide of SEQ ID NO:2 encoding the mature amylase AX856 at three different positions in the chromosome.

*Bacillus licheniformis* JA3720:

A second synthetic codon-optimized gene (Syn2) encoding the AX856 amylase was cloned into a phage integration vector, flanked downstream by an attP site for integration and upstream by the cry3A region, the latter intended for vector-only cross out by homologous recombination after integration of the full construct. The DNA sequence encoding the mature part of the amylase is shown in SEQ ID NO:3. The mature part of the amylase was expressed as a fusion polypeptide with the AmyL signal peptide. The resulting plasmid pJA3692 for inserting the amylase gene behind the triple tandem promoter region at the three attB sites on the parent *B. licheniformis* chromosome. The resulting 3-copy amylase strain was denoted JA3720.

The JA3720 strain has three copies of the synthetic polynucleotide of SEQ ID NO:3 encoding the mature amylase AX856 at three different positions in the chromosome.

*Bacillus licheniformis* JA3722:

A third synthetic codon-optimized gene (Syn3) encoding the AX856 amylase was cloned into a phage integration vector, flanked downstream by an attP site for integration and upstream by the cry/3A region, the latter intended for vector-only cross out by homologous recombination after integration of the full construct. The DNA sequence encoding the mature part of the amylase is shown in SEQ ID NO:4. The mature part of the amylase was expressed as a fusion polypeptide with the AmyL signal peptide. The resulting plasmid pJA3694 for inserting the amylase gene behind the triple tandem promoter region at the three attB sites on the parent *B. licheniformis* chromosome. The resulting 3-copy amylase strain was denoted JA3722.

The JA3722 strain has three copies of the synthetic polynucleotide of SEQ ID NO:4 encoding the mature amylase AX856 at three different positions in the chromosome.

Fermentations:

Fed-batch fermentation with *Bacillus licheniformis* was conducted as described below. All growth media were sterilized by methods known in the art. Unless otherwise described, tap water was used. The ingredient concentrations referred to in the below recipes are before any inoculation.

First Inoculum Medium:

SSB4 agar. Soy peptone SE50MK (DMV) 10 g/l; sucrose 10 g/l; Di-Sodiumhydrogenphosphate, 2H2O 5 g/l; Potassiumdihydrogenphosphate 2 g/l; Citric acid 0.2 g/l; Vitamins (Thiamin-hydrochlorid 11.4 mg/l; Riboflavin 0.95 mg/l; Nicotinic amide 7.8 mg/l; Calcium D-pantothenate 9.5 mg/l; Pyridoxal-HCl 1.9 mg/l; D-biotin 0.38 mg/l; Folic acid 2.9 mg/l); Trace metals (MnSO4, H$_2$O 9.8 mg/l; FeSO4, 7H2O 39.3 mg/l; CuSO4, 5H2O 3.9 mg/l; ZnSO4, 7H2O 8.2 mg/l); Agar 25 g/l. Use of deionized water. pH adjusted to pH 7.3 to 7.4 with NaOH.

Transfer Buffer.

M-9 buffer (deionized water is used): Di-Sodiumhydrogenphosphate, 2H2O 8.8 g/l; Potassiumdihydrogenphosphate 3 g/l; Sodium Chloride 4 g/l; Magnesium sulphate, 7H2O 0.2 g/l.

Inoculum Shake Flask Medium (Concentration is Before Inoculation):

PRK-50: 110 g/l soy grits; Di-Sodiumhydrogenphosphate, 2H2O 5 g/l; pH adjusted to 8.0 with NaOH/H3PO4 before sterilization.

Make-Up Medium (Concentration is Before Inoculation):

Tryptone (Casein hydrolysate from Difco) 30 g/l; Magnesium sulphate, 7H2O 4 g/l; Di-Potassiumhydrogenphosphate 7 g/l; Di-Sodiumhydrogenphosphate, 2H2O 7 g/l; Di-Ammoniumsulphate 4 g/l; Potassiumsulphate 5 g/l; Citric acid 0.78 g/l; Vitamins (Thiamin-hydrochlorid 34.2 mg/l; Riboflavin 2.8 mg/l; Nicotinic amide 23.3 mg/l; Calcium D-pantothenate 28.4 mg/l; Pyridoxal-HCl 5.7 mg/l; D-biotin 1.1 mg/l; Folic acid 2.5 mg/l); Trace metals (MnSO4, H$_2$O 39.2 mg/l; FeSO4, 7H2O 157 mg/l; CuSO4, 5H2O 15.6 mg/l; ZnSO4, 7H2O 32.8 mg/l); Antifoam (SB2121) 1.25 ml/1; pH adjusted to 6.0 with NaOH/H3PO4 before sterilization.

Feed Medium:

Sucrose 708 g/l;

Inoculum Steps:

First the strain was grown on SSB-4 agar slants 1 day at 37° C. The agar was then washed with M-9 buffer, and the optical density (OD) at 650 nm of the resulting cell suspension was measured. The inoculum shake flask (PRK-50) was inoculated with an inoculum of OD (650 nm)×ml cell suspension=0.1. The shake flask was incubated at 37° C. at 300 rpm for 20 hr. The fermentation in the main fermentor (fermentation tank) was started by inoculating the main fermentor with the growing culture from the shake flask. The inoculated volume was 11% of the make-up medium (80 ml for 720 ml make-up media).

Fermentor Equipment:

Standard lab fermentors were used equipped with a temperature control system, pH control with ammonia water and phosphoric acid, dissolved oxygen electrode to measure oxygen saturation through the entire fermentation.

Fermentation Parameters:

Temperature: 38° C.

The pH was kept between 6.8 and 7.2 using ammonia water and phosphoric acid

Control: 6.8 (ammonia water); 7.2 phosphoric acid

Aeration: 1.5 liter/min/kg broth weight

Agitation: 1500 rpm

Feed Strategy:

0 hr. 0.05 g/min/kg initial broth after inoculation 8 hr. 0.156 g/min/kg initial broth after inoculation End 0.156 g/min/kg initial broth after inoculation Experimental Setup:

The cultivation was run for two days with constant agitation, and the oxygen tension was followed on-line in this period. The different strains were compared side by side.

Results:

The amylase yields from the three synthetic coding sequences relative to the yield from the native coding sequence are listed the table below:

|  | JA 3716 (Native) | JA 3718 (syn1) | JA 3720 (syn2) | JA 3722 (syn3) |
|---|---|---|---|---|
| Day 1 | 1 | 1.4 | 1.3 | 2.3 |
| Day 2 | 1 | 1.3 | 1.1 | 2.4 |

The yields in the table clearly show that one of the synthetic amylase-encoding sequences performs surprisingly better than the other two. The "syn3" amylase gene provides a much higher amylase yield than the native encoding gene and almost twice as much as the other two synthetic genes.

The invention claimed is:

1. An isolated synthetic polynucleotide encoding a mature amylase, said polynucleotide comprising the nucleotide sequence shown in SEQ ID NO:4.

2. The isolated synthetic polynucleotide of claim 1 which consists of the nucleotide sequence shown in SEQ ID NO:4.

3. A polynucleotide construct comprising a polynucleotide of claim 2 operably linked to control sequences that provide for its expression in a host cell of choice.

4. The polynucleotide construct of claim 3, wherein the control sequences comprise a polynucleotide region that encodes a signal peptide fused to the N-terminus of the amylase which directs the amylase into the secretory pathway of the host cell.

5. The polynucleotide construct of claim 4, wherein the signal peptide is the amyL signal peptide.

6. A polynucleotide construct comprising a polynucleotide of claim 1 operably linked to control sequences that provide for its expression in a host cell of choice.

7. The polynucleotide construct of claim 6, wherein the control sequences comprise a tandem promoter.

8. The polynucleotide construct of claim 7, wherein the control sequences comprise a polynucleotide region that encodes a signal peptide fused to the N-terminus of the amylase which directs the amylase into the secretory pathway of the host cell.

9. The polynucleotide construct of claim 8, wherein the signal peptide is the amyL signal peptide.

10. A recombinant host cell transformed with or comprising a polynucleotide of claim 1, wherein said host cell produces the mature amylase.

11. The host cell of claim 10, which is a *Bacillus* cell.

12. The host cell of claim 11, which is a *Bacillus licheniformis* cell.

13. The host cell of claim 11, which is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus megaterium, Bacillus pumilus, Bacillus stearothermophilus, Bacillus subtilis*, or *Bacillus thuringiensis* cell.

14. A method for producing a mature amylase, comprising cultivating a host cell of claim 10 under conditions conducive for the expression of the amylase.

15. The method of claim 14, further comprising recovering the amylase.

16. A method for producing a mature amylase, comprising cultivating a host cell of claim 11 under conditions conducive for the expression of the amylase.

17. The method of claim 16, further comprising recovering the amylase.

18. A method for producing a mature amylase, comprising cultivating a host cell of claim 12 under conditions conducive for the expression of the amylase.

19. The method of claim 18, further comprising recovering the amylase.

20. A method for producing a mature amylase, comprising cultivating a host cell of claim 13 under conditions conducive for the expression of the amylase.

* * * * *

SEQUENCE LISTING

```
<160> NUMBER OF SEQ ID NOS: 4

<210> SEQ ID NO 1
<211> LENGTH: 1449
<212> TYPE: DNA
<213> ORGANISM: Bacillus akibai
<220> FEATURE:
<221> NAME/KEY: misc_feature
<222> LOCATION: (1)..(1449)
<223> OTHER INFORMATION: native Bacillus akibai AX856 mature
      amylase-encoding sequence.

<400> SEQUENCE: 1
```

| | |
|---|---|
| caccataatg gtacgaacgg caccttaatg cagtactttg aatggtatct accaaatgac | 60 |
| ggaaaccatt ggaatagatt aaggtctgat gcaagtaacc taaagataaa agggatctca | 120 |
| gcggtttgga ttcctcctgc atggaagggt gcctctcaaa atgatgtggg gtatggtgct | 180 |
| tatgatctgt atgatttagg agaattcaat caaaaaggaa ccattcgtac aaaatatgga | 240 |
| acgcgcaatc agttacaagc tgcggttaac gccttgaaaa gtaatggaat tcaagtgtat | 300 |
| ggcgatgttg taatgaatca taaaggggga gcagacgcta ccgaaatggt taaagcagtt | 360 |
| gaagtaaacc cgaataatag aaatcaagaa gtgtccggtg aatatacaat tgaggcttgg | 420 |
| acaaagtttg actttccagg acgcgctaat actcattcaa acttcaaatg agatggtat | 480 |
| cactttgatg gagtagattg ggatcagtca cgtaagctga acaatcgaat ttataaattc | 540 |
| cgcactaaag cgtgggattg ggaagtcgat acagaattcg gtaactatga ttacctgctt | 600 |
| tatgcagata ttgacatgga tcacccagag gtagtgaatg agctaagaaa ttggggtgtt | 660 |
| tggtatacga atacattagg ccttgatggt tttagaatag atgcagtaaa acatataaaa | 720 |
| tacagctta ctcgtgattg gattaatcat gttagaagtg caattggcaa aaatatgttt | 780 |
| gcggttgcgg aatttggaa aaatgattta ggtgctattg aaaactattt aaacaaaaca | 840 |
| aactggaacc attcagtctt tgatgttccg ctgcacttta acctctatta tgcttcaaaa | 900 |
| agcggaggga attatgatat gaggcaaata tttaatggta cagtcgtgca aaaacatcca | 960 |
| actcatgctg ttacatttgt tgataatcat gattcgcaac ctgaagaatc cttggagtct | 1020 |
| tttgttcgcg aatggttcaa accattagcg tatgctttga cattaacacg tgaacaaggc | 1080 |
| tacccttctg tattttatgg agattattat ggcattccaa cgcatggtgt accagcgatg | 1140 |
| aaatcgaaaa ttgacccgat tttagaagcg cgtcaaaagt atgcatatgg aagacaaaat | 1200 |
| gactacttag accatcataa tatcatcggt tggacacgtg aagggaatac agcacacccc | 1260 |
| aactccggtt tagctactat catgtccgat ggggcaggag gaaataagtg gatgttgtt | 1320 |
| gggcgtaata aagctggtca agtttggacc gatatcaccg gaaataaagc cggtactgtt | 1380 |
| acgattaatg ctgatggatg gggtaatttt tctgtaaatg gaggatcagt ttctatttgg | 1440 |
| gtaaacaaa | 1449 |

<210> SEQ ID NO 2
<211> LENGTH: 1449
<212> TYPE: DNA
<213> ORGANISM: artificial sequence
<220> FEATURE:
<223> OTHER INFORMATION: Synthetic construct

<400> SEQUENCE: 2

| | |
|---|---|
| catcacaacg gaacaaacgg caccctgatg cagtactttg agtggtacct gccgaatgac | 60 |
| ggaaatcatt ggaacagact gcgtagtgat gccagtaacc tgaaggataa gggcatcagc | 120 |
| gctgtgtgga ttcctcctgc ctggaaggga gcatcccaaa acgatgtggg gtatggcgct | 180 |
| tacgatctgt atgatctggg ggagtttaac cagaagggga ccatccgcac gaagtacgga | 240 |
| accagaaacc agctgcaagc agcagtgaac gccctgaaga gtaatggcat ccaggtgtat | 300 |
| ggtgatgtgg tgatgaacca taagggtggt gctgacgcca ccgaaatggt gaaggcagtg | 360 |
| gaagtgaacc cgaacaaccg gaaccaagaa gtgagcggtg aatacaccat cgaggcgtgg | 420 |
| acaaagttcg actttcctgg agagcaaac acacatagca actttaagtg gagatggtat | 480 |
| cattttgatg gtgtgtgattg ggatcagtca cgaaagctga acaacagaat ctataagttt | 540 |
| cgcacaaagg cgtgggattg ggaagtggat actgaatttg gcaactatga ctatctgctg | 600 |

```
tacgccgaca tcgacatgga tcatccggaa gtggtgaacg aactgagaaa ctggggagtg      660
tggtacacca acaccctggg tctggacggt tttcgtatcg acgctgtgaa gcatatcaag      720
tattcattta caagagactg gatcaatcat gtgcgcagcg ctatcggtaa gaatatgttt      780
gctgtggcag agttttggaa gaacgatctg ggagctatcg aaaactatct gaacaagaca      840
aactggaacc atagtgtgtt tgatgtgccg ctgcacttta acctgtacta tgcgagcaag      900
agcggtggga actatgacat gcgtcaaatc ttcaatggca ccgtggtgca aaagcatccg      960
acgcatgcgg tgacttttgt ggataatcac gatagccagc cggaagaaag cctggaaagc     1020
tttgtgcgag aatggtttaa gccgctggct tatgctctga cgctgaccag agaacagggc     1080
tatccgagcg tgttctatgg tgattactac ggaatcccga cgcatggagt gcctgctatg     1140
aagtccaaga tcgatccgat cctggaagcc agacaaaagt atgcctatgg tagacaaaat     1200
gattatctgg accatcataa catcatcggt tggacgagag aaggtaacac agcacatccg     1260
aacagcggac tggctacgat catgagcgat ggagctggtg gtaacaagtg gatgtttgtg     1320
ggaagaaaca aggctggaca ggtgtggacc gatatcacag gcaacaaggc tggtaccgtg     1380
acgatcaacg ctgatggatg gggcaatttc agtgtgaatg gtggtagtgt gagcatctgg     1440
gtgaataag                                                             1449

<210> SEQ ID NO 3
<211> LENGTH: 1450
<212> TYPE: DNA
<213> ORGANISM: artificial sequence
<220> FEATURE:
<223> OTHER INFORMATION: Synthetic construct

<400> SEQUENCE: 3
scatcacaac ggaacaaatg gaacactgat gcagtatttc gagtggtacc tgccgaacga       60
tggcaaccat tggaatcgtc tgcggtcaga tgcgagcaac ctgaaggata agggaatctc      120
agcggtgtgg attcctcctg cgtggaaagg cgcttcacaa aatgatgtgg ggtatggcgc      180
ttatgatctg tatgacctgg gagagttcaa tcaaaagggc acaatcagaa caaagtacgg      240
tacgagaaat caactgcaag cggctgtgaa cgctctgaag tctaacggca tccaagtgta      300
tggtgatgtg gtgatgaacc ataagggagg cgctgatgcc accgagatgg tgaaggcggt      360
ggaggtgaac cccaacaata gaaaccaaga agtgtcaggt gagtacacaa tcgaggcttg      420
gaccaagttt gacttccggg acgagccaa cacgcatagc aatttcaagt ggagatggta      480
tcattttgat ggagtggatt gggaccagag caggaagctg aataaccgga tctacaagtt      540
tcgaaccaag gcttgggact gggaggtgga tacggagttt ggcaactatg attatctgct      600
gtatgctgat atcgatatgg accatccaga agtggtgaat gagctgagaa actggggagt      660
gtggtatact aacacactgg gactggatgg attccgtatc gatgccgtga agcatatcaa      720
gtacagcttc acgagggact ggatcaatca tgtgagatca gccatcggaa gaatatgtt     780 tgctgtggca gagttttgga agaatgatct gggagctatc gagaactatc tgaacaagac      840
caattggaac catagcgtgt tgatgtgcc gctgcatttc aatctgtact atgctagcaa      900
gagcggaggc aactacgata tgagacaaat ctttaacggt acggtggtgc agaagcatcc      960
gacacacgcg gtgacatttg tggataacca cgacagccag ccggaagaat ctctggagag     1020
ctttgtgaga gaatggttca gccgctggct ttatgcactg actctgacta gagaacaagg     1080
atatccgagc gtgttctatg gcgactacta tggaatcccg acccacggtg tgcctgcaat     1140
```

```
gaagtcaaag atcgacccga tcctggaagc tcgacagaag tatgcgtacg ggagacaaaa   1200
cgattacctg gaccaccaca acatcatcgg atggacaaga gagggcaaca ccgctcaccc   1260
gaacagcggt ctggctacaa tcatgagcga tggcgctgga gggaacaagt ggatgtttgt   1320
gggacgcaac aaagctgggc aggtgtggac tgacatcaca ggaaacaaag ccggaacggt   1380
gacaatcaat gcagacggat ggggaaactt tagcgtgaac ggagggtctg tgagcatctg   1440
ggtgaataag                                                          1450

<210> SEQ ID NO 4
<211> LENGTH: 1449
<212> TYPE: DNA
<213> ORGANISM: artificial sequence
<220> FEATURE:
<223> OTHER INFORMATION: Synthetic construct

<400> SEQUENCE: 4
catcataacg gaactaacgg gacactgatg caatacttcg aatggtatct gccgaatgat     60
gggaaccatt ggaatcgcct gagatctgat gctagcaatc tgaaggacaa gggcatcagc    120
gcagtgtgga ttcctcctgc gtggaaggga gctagccaaa cgatgtggg ctacggtgcg    180 tacgacctgt acgacctggg agagttcaac cagaagggaa ccatcagaac aaagtatggg    240
acacggaacc aactgcaagc tgccgtgaac gcgctgaagt ctaatggaat ccaagtgtat    300
ggcgacgtgg tgatgaacca caagggtgga gccgatgcaa ctgaaatggt gaaggctgtg    360
gaagtgaacc ccaacaacag aaatcaggaa gtgagtggtg agtatacaat cgaggcttgg    420
acaaagtttg attttcctgg gagagcaaac acccattcaa actttaagtg gagatggtat    480
cacttcgatg gagtggattg ggaccagagc agaaagctga ataacagaat ctataagttt    540
cgcacaaagg cttgggattg ggaggtggat acagaatttg gcaactatga ttacctgctg    600
tatgctgaca tcgacatgga tcatccggaa gtggtgaacg aactgcggaa ctggggagtg    660
tggtatacca atacactggg actggatggc tttaggatcg acgctgtgaa gcatatcaag    720
tatagcttta ctagagattg gatcaaccac gtgcggagcg ctatcggtaa gaatatgttc    780
gcagtggcag agttttggaa gaacgacctg ggtgcaatcg aaaactatct gaataagacc    840
aactggaacc attcagtgtt tgatgtgccg ctgcatttca acctgtacta tgcgagtaag    900
tcgggtggca attacgacat gagacagatc ttcaatggca cggtggtgca gaagcacccg    960
acgcatgctg tgacgtttgt ggacaaccat gattcccaac cggaggaaag cctggaatct   1020
tttgtgagag aatggtttaa gccgctggct tacgccctga cgctgacgag agagcaaggg   1080
tatccttctg tgttctatgg agactattac ggaatcccga cccacggagt gcctgctatg   1140
aagtcgaaga tcgatccgat cctggaagct agacagaagt atgcttacgg aagacagaac   1200
gattacctgg accaccacaa tatcatcgga tggacgagag aaggcaacac ggctcatccg   1260
aatagtggac tggctacaat catgagcgat ggagctggcg taacaagtg gatgtttgtg   1320 ggacgcaata aggctggaca ggtgtggaca gatatcacag gaaacaaggc tggcacagtg   1380
acgatcaatg ctgacggctg ggggaacttc agcgtgaacg gtgggtcagt gagcatctgg   1440
gtgaacaag                                                          1449
```